United States Patent

Takahashi et al.

[11] Patent Number: 5,504,218
[45] Date of Patent: Apr. 2, 1996

[54] METHOD FOR PRODUCTION PYROMELLITIC ANHYDRIDE

[75] Inventors: Tsukasa Takahashi; Tatsuya Kawabata; Masaaki Okuno; Yasuhisa Emoto; Toshio Sagane; Kenji Ueda, all of Hyogo, Japan

[73] Assignee: Nippon Shokubai Co., Ltd., Osaka, Japan

[21] Appl. No.: 416,229

[22] Filed: Apr. 4, 1995

[30] Foreign Application Priority Data

Apr. 5, 1994 [JP] Japan .................. 6-067209
May 26, 1994 [JP] Japan .................. 6-112645

[51] Int. Cl.$^6$ ........................................ C07D 307/89
[52] U.S. Cl. .................. 549/239; 562/412; 562/413; 562/415
[58] Field of Search ............... 549/239; 562/415, 562/412, 413

[56] References Cited

U.S. PATENT DOCUMENTS

| | | | |
|---|---|---|---|
| 4,665,200 | 5/1987 | Nakanishi et al. | 549/239 |
| 4,694,089 | 9/1987 | Kosaha et al. | 549/239 |
| 4,725,291 | 2/1988 | Ueoka et al. | 549/239 |
| 4,925,957 | 5/1990 | Enomoto et al. | 549/239 |
| 5,387,699 | 2/1995 | Wagner et al. | 549/239 |

FOREIGN PATENT DOCUMENTS

| | | |
|---|---|---|
| 5030838 | 7/1973 | Japan . |
| 415020 | 7/1984 | Japan . |
| 413026 | 7/1984 | Japan . |
| 1245857 | 3/1988 | Japan . |
| 3-294272 | 12/1991 | Japan ............ 549/239 |
| 5-1069 | 1/1993 | Japan ............ 549/239 |
| 72864 | 2/1994 | Japan . |
| 1031121 | 11/1989 | U.S.S.R. ......... 549/239 |

*Primary Examiner*—Cecilia Tsang
*Attorney, Agent, or Firm*—Omri M. Behr; Matthew J. McDonald

[57] ABSTRACT

A method for producing efficiently on a commercial scale pyromellitic anhydride having high purity and suffering only sparing coloration in a high yield from a raw material of high concentration is provided. By the use of a multilayer catalyst formed by packing on the reaction gas outlet side a first catalyst containing V and Mo and/or W and having an atomic ratio of Mo and/or W to V in the range of from 0.01 to 2, on the raw material mixed gas inlet side a second catalyst containing V, Mo and/or W and having an atomic ratio of Mo and/or W to V smaller than the atomic ratio of the first catalyst, and/or a third catalyst containing V and an alkali metal and having an atomic ratio of the alkali metal to V in the range of from 0.2 to 2.5, pyromellitic anhydride is produced by the vapor-phase oxidation of a tetraalkyl benzene with a molecular oxygen-containing gas.

15 Claims, 1 Drawing Sheet

METHOD FOR PRODUCTION PYROMELLITIC ANHYDRIDE

BACKGROUND OF THE INVENTION

1. Field of the Invention

This invention relates to a method for the production of pyromellitic anhydride from a tetraalkyl benzene by the catalytic vapor-phase oxidation technique. Pyromellitic anhydride is used for heat-resistant resins, plasticizers, epoxy resin curing agents, etc. and is useful as various industrial materials.

2. Description of the Prior Art

Various methods have been heretofore proposed for the production of pyromellitic anhydride. Various methods of catalytic vapor-phase oxidation of 1,2,4,5-tetraalkyl benzenes discloses in JP-B-49-9,451 and JP-B-04-15,020, a method of liquid-phase oxidation of a 1,2,4,5-tetraalkyl benzene (JP-A-61-27,942), a method of liquid-phase oxidation of a 2,4,5-trimethyl benzaldehyde (JP-A-57-38,745, etc.), and a method of catalytic vapor-phase oxidation of anthracene (JP-A-56-8,388, etc.) are examples. Among other methods cited above, the method of catalytic vapor-phase oxidation of a 1,2,4,5-tetraalkyl benzene has been drawing attention as a process capable of inexpensively producing pyromellitic anhydride on a quantity basis because a zeolite type catalyst recently developed for use in the catalytic vapor-phase oxidation under consideration has opened up the possibility that the raw material 1,2,4,5-tetraalkyl benzene which has been heretofore expensive will be procured abundantly and inexpensively.

The catalysts proposed to date for use in the production of pyromellitic anhydride by the catalytic vapor-phase oxidation of tetraalkyl benzenes include $V_3O_5$—$TiO_2$, $WO_2$ type (Belgian Patent No. 655686), $V_2O_5$—$P_2O_5$—$TiO_2$, $MoO_3$, $WO_3$ (JP-B-45-4,978), $V_2O_5$—$TiO_2$ (anatase type)-$MoO_3$, $P_2O_5$ (JP-B-45-15,018), $V_2O_5$—$TiO_2$—$Na_2O$—$P_2O_5$ type (JP-B-45-15,252), $V_2O_5$—$MoO_3$—$P_2O_5$ (JP-B-47-30,821), $V_2O_5$—$TiO_2$—$P_2O_5$—$Nb_2P_5$—$K_2O$, $P_2O_5$, $TiO_2$, $Na_2O$ (JP-B-49-31,973), and $V_2O_5$—$B_2O_5$ (JP-B-48-35,251), $V_2O_5$—$Na_2O$—$MoO_3$— Cr, Mn, Nb (JP-A-01-294,679), for example.

As examples of an operation which uses two or more divided catalyst beds per production unit, U.S. Pat. No. 4,665,200, etc. disclose methods which repress the amount of reaction at the hot spot of a catalyst bed by such measures as diluting a catalyst with a carrier, enlarging the diameter of component beads of a catalyst, decreasing the amount of a catalyst deposited on a carrier, decreasing the content of vanadium, an alkali metal, or phosphorus, or decreasing the specific surface area of $ZrO_2$, $TiO_2$, or $SnO_2$ for the purpose of lowering the temperature of the hot spot.

As an example of an operation which uses a plurality of species of catalyst unlike divided catalyst beds, JP-A-50-30,838 discloses a method for producing pyromellitic anhydride of high purity by a procedure which comprises first forming a gas in a reaction vessel and then passing the formed gas through an aftertreating vessel packed with a catalyst having a different composition from the catalyst used in the reaction vessel thereby disposing of a secondary product of the reaction.

The reaction for converting a tetraalkyl benzene into pyromellitic anhydride inherently entails oxidation of four alkyl groups. It is inferred, therefore, that this reaction proceeds through a reaction path more complicated and greater in number of stages than the conventional reaction as in the production of phthalic acid from orthoxylene. Further, as the precursor of pyromellitic anhydride which is an intermediate oxide, the presence of aldehydes and dimethyl phthalic acid having two of the four alkyl groups thereof already oxidized has been demonstrated. In spite of these facts, a method embodying an idea of using as many catalyst beds as reaction stages which are involved in the production of pyromellitic anhydride by the catalytic vapor-phase oxidation of a tetraalkyl benzene has never been disclosed to date.

Since the conventional methods utilize practically one species of catalyst for effecting many separate reaction stages, they entrain various problems such as unduly low concentration of tetraalkyl benzene in the composition of the raw material gas, insufficient selectivity of the conversion of tetraalkyl benzene to pyromellitic anhydride, necessitation of a refining step for a product so defiled as to assume a color or suffer from unduly low purity notwithstanding such other conditions as mentioned above are rather satisfactory. Thus, these conventional methods do not prove fully satisfactory from the industrial point of view.

Even catalysts which satisfy these conditions to a rather large extent have their performances based on a delicate balance of their characteristic properties manifested to a plurality of reactions, their performances tend to fluctuate. The catalysts themselves, therefore, are difficult to manufacture.

An object of this invention, therefore, is to provide a novel method for the production of pyromellitic anhydride.

Another object of this invention, in association with the production of pyromellitic anhydride by the catalytic vapor phase oxidation of a raw material mixed gas comprising of a tetraalkyl benzene and a molecular oxygen-containing gas, is to provide a method for the production of pyromellitic anhydride of high purity efficiently from the viewpoint of commercial production and in a high yield by using a catalyst system which combines specific catalysts.

Yet another object of this invention is to provide a method for producing pyromellitic anhydride of sparing coloration and high purity at a high raw material concentration by the catalytic vapor-phase oxidation of a tetraalkyl benzene.

SUMMARY OF THE INVENTION

The various objects mentioned above are accomplished by a method for the production of pyromellitic anhydride by the catalytic vapor-phase oxidation of a raw material mixed gas comprising a tetraalkyl benzene and a molecular oxygen-containing gas by the use of a fixed-bed shell-and-tube type reaction vessel, which comprises using a multilayer catalyst obtained by dividing a catalyst layer to be used in the reaction vessel into at least two layers, packing the produced gas outlet side thereof with a first catalyst containing vanadium (a) and at least one metal (b) selected from the group consisting of molybdenum and tungsten and having an atomic ratio of the metal (b) to vanadium (a) in the range of from 0.01 to 2, and packing the raw material mixed gas inlet side thereof with at least one other species of catalyst selected from the group consisting of a second catalyst containing vanadium (a) and at least one metal (b) selected from the group consisting of molybdenum and tungsten and having an atomic ratio of the metal (b) to vanadium (a) smaller than the first catalyst and a third catalyst containing vanadium (a) and an alkali metal (c) and having a ratio of the alkali metal (c) to vanadium (a) in the range of from 0.2 to 2.5.

This invention further pertains to the aforementioned method, wherein a packed volume of the first catalyst is greater than a packed volume of the second catalyst. This invention further pertains to the aforementioned method, wherein the first catalyst further contains silver and the atomic ratio of silver to vanadium is in the range of from 0.001 to 0.2. This invention further pertains to the aforementioned method, wherein the first catalyst further contains at least one metal selected from the group consisting of alkali metals and alkaline earth metals and the atomic ratio of the metal to vanadium is in the range of from 0.001 to 0.1. This invention further pertains to the aforementioned method, wherein the first catalyst further contains at least one element selected from the group consisting of phosphorus, antimony, boron, chromium, cerium, and sulfur and the atomic ratio of the element to vanadium is in the range of from 0.002 to 1. This invention further pertains to the aforementioned method, wherein the first catalyst has the catalytically active components thereof dispersed in a powder or whiskers of an inorganic oxide. This invention further pertains to the aforementioned method, wherein the second catalyst has the catalytically active components thereof dispersed in a powder or whiskers of an inorganic oxide. This invention further pertains to the aforementioned method, wherein the second catalyst further contains at least one element selected from the group consisting of phosphorus, antimony, boron, chromium, cerium and sulfur and the atomic ratio of the element to vanadium is in the range of from 0,002 to 1. This invention further pertains to the aforementioned method, wherein the third catalyst further contains at least one element selected from the group consisting of silver, sulfur, boron, tantalum, and molybdenum and the atomic ratio of the element to vanadium is in the range of 0.01 to 2. This invention further pertains to the aforementioned method, wherein the third catalyst further contains at least one element selected from the group consisting of phosphorus and copper, and the atomic ratio of the element to vanadium is in the range of more than 0 to not more than 2. This invention further pertains to the aforementioned method, wherein the third catalyst further contains at least one element selected from the group consisting of silver, sulfur, boron, tantalum, and molybdenum and the atomic ratio of said element to vanadium is in the range of from 0.01 to 2. This invention further pertains to the aforementioned method, wherein the concentration of the tetraalkyl benzene in the raw material mixed gas is in the range of from 10 to 100 g/Nm$^3$ and the reaction temperature is in the range of from 340° to 460° C. This invention further pertains to the aforementioned method, wherein the first catalyst is packed in an amount such as to produce a space velocity in the range of from 2,000 to 20,000 hr$^{-1}$, the second catalyst is packed in an amount such as to produce a space velocity in the range of from 10,000 to 50,000 hr$^{-1}$, and the third catalyst is packed in an amount such as to produce a space velocity in the range of from 500 to 50,000 hr$^{-1}$.

The method of this invention produces pyromellitic anhydride by subjecting a tetraalkyl benzene to vapor-phase oxidation with a molecular oxygen-containing gas in the presence of a multilayer catalyst obtained by packing the produced gas outlet side of a reaction vessel with a first catalyst containing V and Mo and/or W and having an atomic ratio of Mo and/or W to V in the range of from 0.01 to 2 and the raw material mixed gas inlet side of the reaction vessel with a second catalyst containing V and Mo and/or W and having an atomic ratio of Mo and/or W to V smaller than the first catalyst and/or a third catalyst containing V and an alkali metal and having an atomic ratio of the alkali metal to V in the range of from 0.2 to 2.5 as described above. It, therefore, can manufacture the product with a high purity in a high yield efficiently from the operational point of view. It can obtain pyromellitic anhydride of high purity with slightly coloration from the raw material which is used in a high concentration.

EXPLANATION OF THE PREFERRED EMBODIMENT

This invention, as described above, concerns a method for the production of pyromellitic anhydride by the catalytic vapor phase oxidation of a raw material mixed gas comprising a tetraalkyl benzene and a molecular oxygen-containing gas by the use of a fixed-bed shell-and-tube type reaction vessel, which comprises using a multilayer catalyst obtained by dividing a catalyst layer to be used in the reaction vessel into at least two layers, packing the produced gas outlet side thereof with a first catalyst containing vanadium (a) and at least one metal (b) selected from the group consisting of molybdenum and tungsten and having an atomic ratio of the metal (b) to vanadium (a) in the range of from 0.01 to 2, and packing the raw material mixed gas inlet side thereof with at least one other species of catalyst selected from the group consisting of a second catalyst containing vanadium (a) and at least one metal (b) selected from the group consisting of molybdenum and tungsten and having an atomic ratio of the metal (b) to vanadium (a) smaller than the first catalyst and a third catalyst containing vanadium (a) and an alkali metal (c) and having a ratio of the alkali metal (c) to vanadium (a) in the range of from 0.2 to 2.5.

Now, this invention will be described more specifically below.

First, the method for packing a catalyst which constitutes itself an important feature of this invention will be explained in greater detail.

In the actual packing of the reaction vessel with the first catalyst (A), the second catalyst (B), and the third catalyst (C) mentioned above, the three cases illustrated in FIGS. 1 through 3 (the raw material gas inlet side on the left and the produced gas outlet side on the right in the bearings of the diagrams) are conceivable.

The fact that the first catalyst (A) is invariably installed on the produced gas outlet side characterizes this invention.

Figure 1:
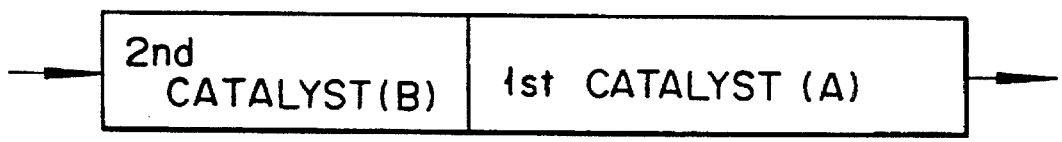
FIG. 1 is a block diagram showing one example of the catalyst bed layout in the method of this invention.

In the case of a two-layer catalyst shown in FIG. 1, since the second catalyst (B) exhibiting higher activity to tetraalkyl benzene than the first catalyst (A) is packed on the raw material gas inlet side of the reaction vessel, the drawback of the first catalyst (A) is made up by the second catalyst (B) taking the place of the first catalyst (A) in executing the reaction of the tetraalkyl benzene of a high concentration at a low temperature. This layout of the catalysts, therefore, brings about an effect of heightening the yield and, at the same time, permits stabilization of the performance of the catalyst system as a whole.

Figure 2:
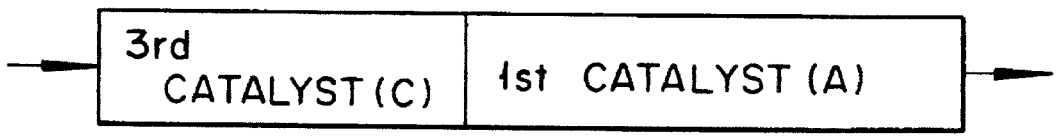
FIG. 2 is a block diagram showing another example of the catalyst bed layout in the method of this invention.

In the case of a two-layer catalyst shown in FIG. 2, the fact that the third catalyst (C) which is capable of selectively forming an intermediate oxide destined to serve as a precursor of the pyromellitic anhydride is packed on the raw material mixed gas inlet side of the reaction vessel allows a decrease in the amount of the tetraalkyl benzene to be introduced into the first catalyst (A), ensures formation of the product at a high yield by virtue of the characteristic quality of the first catalyst (A) effecting the conversion of the intermediate oxide into pyromellitic anhydride at high selectivity, and also curbs coloration of the product.

Figure 3:
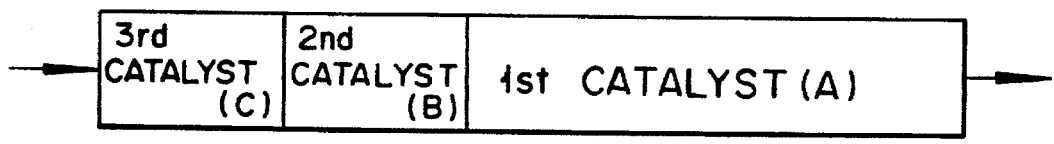
FIG. 3 is a block diagram showing yet another example of the catalyst bed layout in the method of this invention.

In the case of a three-layer catalyst shown in FIG. 3, since the second catalyst (B) is packed on the raw material mixed gas inlet side of the first catalyst (A) and the third catalyst (C) is packed at the position in front of that of the first catalyst (A), the product is formed at a still higher yield and the coloration is curbed to a still greater extent owing to the combination of the effects of the two cases mentioned above.

A layer length ratio of the first catalyst and the second catalyst is that the layer length of the first catalyst is larger than the layer length of the second catalyst as a substantial catalyst layer length excluding a carrier for dilution in the catalyst layer using the second catalyst. Activity of the second catalyst can be controlled by varying a supported amount, a specific surface area of the inorganic powder, and amount of the use of the catalyst, and adding an additive in addition to dilution by the carrier, but it is difficult to define the layer length. However, the length range of the second catalyst layer/the first catalyst layer=1/10 though 1/1, preferably the second catalyst layer/the first catalyst layer=1/8 through 1/2 is preferably used as a substantial layer length excluding a carrier for dilution.

A layer length of the third catalyst is effective in the range of not less than 1/5 of the first catalyst in case of aiming the effect of removing color, but it is preferable to pack the more amount in order to increase the effect of the high yield, and the upper limit is substantially decided by an apparatus and economical conditions. Further, when the second catalyst is used at the same time, 1/5 though 1/2 of the packed amount is sufficient, because effect of increase of yield is small even if the amount is increased.

These methods of catalyst packing are selectively adopted, depending on such factors as economic environment and production facilities.

In the specification of this invention, the first catalyst (A), the second catalyst (B), and the third catalyst (C) will be severally described as being formed of a single catalyst. The part of the first catalyst (A) shown in the diagrams mentioned above, when desired, may be split into a plurality of portions of first catalyst (A) in which the atomic ratio of molybdenum and/or tungsten to vanadium sequentially increased in the direction from the raw material mixed gas inlet side to the reaction gas outlet side. By the same token, the part of the third catalyst (C) shown in the diagrams may be split into a plurality of portions of third catalyst (C) in which the atomic ratio of the alkali metal to vanadium sequentially decreased in the direction from the raw material mixed gas inlet side to the reaction gas outlet side. These modifications are embraced by the present invention.

The method of packing in the case of the layout of FIG. 1 will be described in greater detail.

Since the amounts of the second catalyst (B) and the first catalyst (A) to be packed are affected by the characteristics of the catalysts and the characteristics of the reaction vessel to be used, they are preferable to be properly selected to suit the occasion. Generally, the amount of the second catalyst (B) to be packed is such that the packed portion may allow a space velocity in the range of from 10,000 to 50,000 hr$^{-1}$ preferably from 15,000 to 40,000 hr$^{-1}$ and the amount of the first catalyst (A) to be packed is such that the packed portion may allow a space velocity in the range of from 2,000 to 20,000 hr$^{-1}$, preferably from 3,000 to 15,000 hr$^{-1}$.

The amount of the second catalyst (B) to be packed is an important magnitude; the yield abruptly falls when this amount is smaller than a specific minimum and the yield also falls when the amount exceeds a specific optimum. The effect of this magnitude, however, is not particularly acute. Such a fluctuation of the amount of this catalyst as is practically equivalent to an error incurred at the time of packing produces virtually no effect. The smallest amount of the second catalyst (B) to be packed may be decided on the rule that it be such that the position in the catalyst bed at which the highest temperature exists in the temperature distribution in the catalyst bed falls at the position at which the second catalyst (B) is packed. At the position at which the second catalyst (B) is packed, the conversion of the raw material tetraalkyl benzene is not less than 50% and less than 100%, preferably not less than 70% and less than 100%. As respects the amount of the first catalyst (A) to be packed, if this amount is less than the lower limit of the range mentioned above, the reaction will be at a disadvantage in increasing the content of impurities in the product. If this amount exceeds the upper limit of the range, the excess will be wasted and will further entrain the disadvantage of increasing the resistance which the catalyst bed offers to the flow of gas therethrough.

As a measure beneficial to the packing of the catalyst, a method which comprises diluting a catalyst bed as with a carrier for the purpose of lowering the highest temperature of the catalyst bed may be effectively utilized herein. Naturally, the space velocity in the diluted catalyst bed must be lower than that in the catalyst bed which is not diluted. The space velocity may fall short of reaching the lower limit of the range mentioned above, depending on the degree to which the dilution has been made.

As another measure beneficial to the packing of the catalyst, a method which comprises disposing between the second catalyst (B) and the first catalyst (A) a separation layer formed of an inert carrier or the like may be utilized herein. This method is effective in preventing each of the catalysts from being defiled by the other catalyst of a different composition.

When the catalysts are packed as described above, the product can be obtained at a high yield and, at the same time, the stability of the catalyst system as a whole can be improved as compared with the first catalyst (A) and the second catalyst (B) which are used independently of each other.

Now, the method of packing in the case of the layout of FIG. 2 will be described in greater detail.

The amounts of the first catalyst (A) and the third catalyst (C) to be packed are preferable to be large because the effect of heightening the yield of pyromellitic anhydride is exalted by increasing the conversion of tetraalkyl benzene in the third catalyst (C). With due respect to the economy, the third catalyst (C) is generally packed in an amount such that the site of packing allows a space velocity in the range of from 500 to 50,000 hr$^{-1}$, preferably from 1,000 to 30,000 hr$^{-1}$. If the amount of this catalyst is smaller than the lower limit of the range mentioned above, the conversion in the catalyst of the preceding stage will be insufficient and the effect of the third catalyst (C) will not fully manifest the effect thereof.

Conversely, if this amount exceeds the upper limit of the range, the catalyst bed will offer unduly high resistance to passage of gas and render the production uneconomical.

The amount of the first catalyst (A) to be packed is generally such that the layer of the packed catalyst (A) may allow a space velocity in the range of from 1,000 to 15,000 hr$^{-1}$ preferably from 3,000 to 10,000 hr$^{-1}$ of the catalyst is smaller than the lower limit of this range, the amount of the secondary product of the reaction will increase. If this amount is larger than the upper limit of the range, the yield of the pyromellitic anhydride will be unduly small.

As yet another measure beneficial to the packing of the catalyst, a method which comprises diluting a catalyst bed as with a carrier for the purpose of lowering the highest temperature of the catalyst bed may be effectively utilized herein. Naturally, the space velocity in the diluted catalyst bed must be lower than that in the catalyst bed which is not diluted. The space velocity may fall short of reaching the lower limit of the range mentioned above, depending on the degree to which the dilution has been made.

As another measure beneficial to the packing of the catalyst, a method which comprises disposing between the first catalyst (A) and the third catalyst (C) a separation layer formed of an inert carrier or the like may be utilized herein. This method is effective in preventing each of the catalysts from being defiled by the other catalyst of a different composition.

Having the catalysts packed in such a manner as is described above brings about the effect of improving the yield with a margin of from 2 to 7 mol % over the first catalyst (A) which is packed by itself and repressing the coloration of the product.

Finally with respect to the case of FIG. 3, the method of packing will be described more specifically below.

The method shown in FIG. 3 resides in producing a structure in which the third catalyst (C) is additionally packed in a small amount on the raw material mixed gas inlet side of the second catalyst (B) disposed in the structure shown in FIG. 1. The third catalyst (C) is generally packed so that the layer of the packed catalyst may allow a space velocity in the range of from 5,000 to 50,000 hr$^{-1}$, preferably from 10,000 to 30,000 hr$^{-1}$. In the structure of FIG. 3, the conversion at the third catalyst (C) does not need to be particularly increased because the intermediate oxide formed in the third catalyst (C) is consumed by the second catalyst (B) before it is supplied to the first catalyst (A) and further because the amount of tetraalkyl benzene to be supplied to the first catalyst (A) is decreased by the second catalyst (B). The third catalyst (C) packed in a smaller amount than in the structure of FIG. 2 suffices to manifest the expected function. If it is packed in a large excess, the excess will not manifest any marked effect. It is, therefore, desired to be used in an amount of the irreducible minimum.

The amounts of the first catalyst (A) and the second catalyst (B) to be packed are equal to those already described with respect to the structure of FIG. 1. The amount of the second catalyst (B) to be packed is such that the layer of the packed catalyst may allow a space velocity in the range of from 10,000 to 50,000 hr$^{-1}$ preferably from 15,000 to 40,000 hr$^{-1}$. The amount of the first catalyst (A) to be packed is such that the layer of the packed catalyst may allow a space velocity in the range of from 2,000 to 20,000 hr$^{-1}$ preferably from 3,000 to 15,000 hr$^{-1}$ When the three catalysts are packed as described above, the third catalyst (C) so functions as to improve the yield with a margin of about 1 mol % over that obtained in the structure of FIG. 1 and decrease the coloration of the product.

Now, the catalysts used in the structure under discussion will be described below.

The first catalyst (A) has vanadium and molybdenum and/or tungsten as essential components thereof. The amounts of molybdenum and tungsten to be used are selected in the range of from 0.01 to 2, preferably from 0.05 to 1, by atomic ratio. When the first catalyst (A) contains molybdenum and/or tungsten in amounts falling in the range mentioned above, the selectivity of the conversion from such intermediate oxides of dimethyl phthalic acid and aldehydes to pyromellitic anhydride can be heightened and the action of reoxidizing the formed pyromellitic anhydride can be repressed to an extremely low level.

As an arbitrary component element for the first catalyst (A) of this invention, the addition of silver proves desirable. The amount of silver to be added is in the range of from 0.001 to 0.2, preferably from 0.01 to 0.2, as the atomic ratio of silver to vanadium. When silver is added within the range mentioned above, it is effective in heightening the activity of the catalyst and, at the same time, curbing the occurrence of a combustion gas and improving the selectivity of the conversion to pyromellitic anhydride. When silver is added in an amount falling outside the range, the selectivity of the conversion to pyromellitic anhydride is lowered. If it is added in an excess amount, the excess will rather enhance the occurrence of a combustion gas.

As another arbitrary component element for the first catalyst (A) of this invention, at least one element selected from the group consisting of alkali metals and alkaline earth metals is used. The amount of this element to be added is in the range of from 0.001 to 0.1, preferably from 0.001 to 0.05, as the atomic ratio to vanadium. The alkali metal and the alkaline earth metal, when added in such a small amount as mentioned above, is effective in improving the yield of pyromellitic anhydride. If they are used in an excess amount, the excess will conspicuously lower the activity of the catalyst and, at the same time, increase the ratio of occurrence of a combustion gas.

As yet another arbitrary component element for the first catalyst (A) of this invention, at least one element selected from the group consisting of phosphorus, antimony, boron, chromium, cerium, and sulfur is used. The addition of phosphorus and/or antimony proves particularly effective. The amount of this element is in the range of from 0.002 to 1, preferably from 0.01 to 1, as the atomic ratio to vanadium. Phosphorus and/or antimony, when added in a suitable amount, is capable of enhancing the yield of pyromellitic anhydride. If it is added in an amount falling outside the range mentioned above, the yield of pyromellitic anhydride will be lowered. If it is added in an excess amount, the excess will rather aggravate the occurrence of a combustion gas.

As a dispersing powder for the active substance, titanium oxide, tin oxide, zirconium oxide, or the like can be used. When the dispersing powder is incorporated in the catalyst, the separation of the active substance from the carrier can be repressed. It can be used for the purpose of decreasing the amount of the active substance which is relatively expensive.

The dispersing powder is not particularly restricted as to the method for preparation or the raw material. It can be prepared by any of the methods which have been generally adopted heretofore. It can be prepared from such raw materials as nitrates, carbonates, and organic acid salts which are decomposed by heating into respective oxides. Titanium oxide, tin oxide, and zirconium oxide are prepared from the corresponding salts prior to the preparation of a relevant catalyst and are used in the form of a calcined oxide powder. The calcined oxide powder can be used particularly advantageously when it has a Brunauer-Emett-Teller (BET) surface area in the range of from 5 to 100 $m^2/g$, preferably from 5 to 40 $m^2/g$. As respects the method for the preparation of the catalyst, the component elements are preferable to be mixed as uniformly as possible. Specifically, the catalyst is produced by mixing or kneading by the use of a stirrer the components prepared in a prescribed formulation in such a solvent as water and depositing the resultant liquid or slurry mixture on a carrier. In this case, the method which enhances the strength with which the slurry mixture is deposited on the carrier by adding whiskers or other similar fibrous substance to the slurry may be used favorably.

The first catalyst (A) may use a carrier. Any of the inert carriers of the common run can be used. Preferably, an inorganic porous carrier which has an apparent porosity in the range of from 5 to 50%, a BET specific surface area of not more than 5 $m^2/g$, preferably from 0.05 to 1 $m^2/g$, an aluminum content of not more than 10% by weight, preferably not more than 3% by weight, and a SiC content of not less than 50% by weight, preferably not less than 80% by weight is used. A self-sintering type porous SiC carrier having an assay of about 98% is advantageously used. The form of the carrier to be used for the first catalyst (A) is not particularly restricted. The carrier may be in any of various forms such as, for example, spheres, rings, cylinders, cones, and saddles. For the carrier to be advantageously used, the apparent outside diameter thereof is desired to be in the range of from 3 to 15 mm, preferably from 3 to 10 mm, on the average.

The deposition of the active substance for the first catalyst (A) on the carrier thereof may be effected by any of the well—known methods such as, for example, the spray deposition method and the impregnation deposition method. Desirably, this deposition of the active substance is carried out by spraying the catalyst solution or catalyst slurry on the carrier which is kept heated at a temperature in the range of from 90° to 350° C., preferably from 200° to 350° C. The amount of the active substance for the catalyst to be deposited is in the range of from 3 to 100 g, preferably from 5 to 30 g, per 100 cc of the apparent volume of the carrier. The active substance thus deposited on the carrier is calcined at a temperature in the range of from 300° to 650° C., preferably from 400° to 600° C., for a period in the range of from 1 to 10 hours, preferably from 2 to 6 hours, to obtain the catalyst.

The first catalyst (A) prepared as described above, owing to the action of molybdenum and tungsten, exhibits only a low oxidizing activity to pyromellitic anhydride, imparts a high selectivity to the conversion of intermediate oxides to pyromellitic anhydride, and enjoys a particularly high quality as a catalyst to be disposed in the rear part of a catalyst bed.

Then, the second catalyst (B) which is packed more on the raw material gas inlet side than the first catalyst (A) and is defined as having a smaller atomic ratio of molybdenum and tungsten to vanadium than the first catalyst (A) will be more specifically described hereinbelow.

The second catalyst (B) has the function of decreasing the amount of a tetraalkyl benzene to be introduced into the first catalyst (A). The vanadium type catalyst which has been used heretofore for the production of pyromellitic anhydride can be used as the second catalyst (B). It is preferable to have a higher activity, particularly at low temperatures, on the tetraalkyl benzene than the first catalyst (A).

As an arbitrary component element for the second catalyst (B), at least one element selected from the group consisting of phosphorus, antimony, boron, chromium, cerium, and sulfur is used. The addition of phosphorus and/or antimony is particularly effective, and especially addition of only antimony is more effective. Preferably, the amount of this element is in the range of from 0.002 to 1, preferably from 0.01 to 10, as the atomic ratio to vanadium. Phosphorus and/or antimony, when added in a proper amount, can improve the yield of pyromellitic anhydride. If it is added in an amount falling outside the range mentioned above, however, the yield of pyromellitic anhydride is lowered.

The second catalyst (B) in a preferred form comprises a catalyst containing the component elements mentioned above and at least one oxide selected from the group consisting of titanium oxide, zirconium oxide, and tin oxide. The oxide properly exalts the activity of the catalyst and enables pyromellitic anhydride to be obtained in a high yield when the content of this oxide is such that the surface area of the oxide is more than 0 and not more than $1 \times 10^5$ $m^2/mol$, preferably from $1 \times 10^2$ to $1 \times 10^4$ $m^2/mol$, of vanadium which is one of the component elements of the catalyst. The oxide is particularly Preferable to contain at least titanium oxide.

The oxide is not particularly restricted as to the method for preparation or the raw material. It can be prepared by any of the methods which have been generally adopted heretofore. It can be prepared from such raw materials as nitrates, carbonates, and organic acid salts which are decomposed by heating into respective oxides. Titanium oxide, tin oxide, and zirconium oxide are prepared from the corresponding salts prior to the preparation of a relevant catalyst and are used in the form of a calcined oxide powder. The calcined oxide powder can be used particularly advantageously when it has a BET surface area in the range of from 5 to 100 $m^2/g$, preferably from 5 to 40 $m^2/g$. As respects the method for the preparation of the catalyst, the component elements are preferable to be mixed as uniformly as possible. Specifically, the catalyst is produced by mixing or kneading by the use of a stirrer the components prepared in a prescribed formulation in such a solvent as water and depositing the resultant liquid or slurry mixture on a carrier. In this case, the method which enhances the strength with which the slurry mixture is deposited on the carrier by adding whiskers or other similar fibrous substance to the slurry may be used favorably.

The second catalyst (B) may use a carrier. Any of the inert carriers of the common run can be used. Desirably, an inorganic porous carrier which has an apparent porosity in the range of from 5 to 50%, a specific surface area of not more than 5 $m^2/g$, preferably not more than 1 $m^2/g$, an aluminum content of not more than 10% by weight, preferably not more than 3% by weight, and a SiC content of not less than 50% by weight, preferably not less than 80% by weight is used. A self-sintering type porous SiC carrier having an assay of about 98% is advantageously used. The form of the carrier to be used for the second catalyst (B) is not particularly restricted. The carrier may be in any of various forms such as, for example, spheres, rings, cylinders, cones, and saddles. For the carrier to be advantageously used, the apparent outside diameter thereof is desired to be in the range of from 3 to 15 mm, preferably from 3 to 10 mm, on the average.

The deposition of the active substance for the second catalyst (B) on the carrier thereof may be effected by any of the well-known methods such as, for example, the spray deposition method and the impregnation deposition method. Preferably, this deposition of the active substance is carried out by spraying the catalyst solution or catalyst slurry on the carrier which is kept heated at a temperature in the range of from 90° to 350° .C, preferably from 100° to 300° C. The amount of the active substance for the catalyst to be deposited is in the range of from 3 to 100 g, preferably from 5 to 30 g, per 100 cc of the apparent volume of the carrier. The active substance thus deposited on the carrier is calcined at a temperature in the range of from 300° to 650° C., preferably from 400° to 600° C., for a period in the range of from 1 to 10 hours, preferably from 2 to 6 hours, to obtain the catalyst.

The second catalyst (B) which is obtained as described above functions to compensate such drawbacks of the first catalyst (A) as low activity on the tetraalkyl benzene and low selectivity particularly in the part of low temperature. By being disposed more on the raw material gas inlet side than the first catalyst (A), this second catalyst (B) is enabled to perform the reaction of a raw material having a high tetraalkyl benzene content at a low temperature on behalf of the first catalyst (A).

Now, the third catalyst (C) which is packed more on the raw material gas inlet side than the first catalyst (A) and which contains vanadium and an alkali metal element and has the atomic ratio of the alkali metal element to vanadium in the range of from 0.2 to 2.5 will be described more specifically below. The third catalyst (C) is aimed at decreasing the amount of a tetraalkyl benzene introduced into the first catalyst (A) and forming an useful intermediate oxide and supplying this oxide to the first catalyst (A).

The compositional characteristic of the third catalyst (C) consists in the fact that the alkali metal content in the catalyst relative to vanadium is higher than that in the conventional alkali metal-incorporating catalyst used for the production of pyromellitic anhydride. This catalyst in itself, therefore, has a very weak ability or practically no ability to form pyromellitic anhydride. The third catalyst (C) which functions as a precedent catalyst in this invention has vanadium and an alkali metal as essential component elements and the atomic ratio of the alkali metal to vanadium in the range of from 0.2 to 2.5, preferably from 0.3 to 1.0, and more preferably from 0.3 to 0.8. If this atomic ratio exceeds the upper limit of the range mentioned above, the catalyst will manifest extremely low catalytic activity and functions insufficiently as a preceding catalyst. If it is short of the lower limit of the range, the amount of the combustion gas to be formed will be so large as to prevent the catalyst from producing the expected effect and possibly induce a decline of the yield.

As an arbitrary component element of the third catalyst (C) in this invention, at least one element selected from the group consisting of phosphorus and copper is used when necessary. The amount of this element to be used is in the range of from 0 to 2, preferably from 0.2 to 1.5, as the atomic ratio to vanadium. This element, when added in a suitable amount, functions to exalt the activity of the catalyst without noticeably increasing the amount of a combustion gas to be formed.

As another arbitrary component element of the third catalyst (C) in this invention, at least one element selected from the group consisting of silver, sulfur, boron, tantalum, and molybdenum is used when necessary. This element, when added in a suitable amount, functions to enhance the activity of the catalyst without noticeably increasing the amount of a combustion gas to be formed.

The third catalyst (C) in a preferred form comprises a catalyst containing the component elements mentioned above and an inorganic powder intended for dispersing the catalytically active substance. The inorganic powder is preferable to be an inactive substance. It may be a thermally stable inorganic powder containing silicon, for example. As typical examples of the inorganic powder, such natural minerals as crystalline silica, amorphous silica, silicon carbide, mullite, cordierite, and diatomaceous earth may be cited. Among other inorganic powders mentioned above, such inexpensive natural minerals as diatomaceous earth can be advantageously used. When the third catalyst (C) incorporates the inorganic powder, it acquires a properly heightened activity and further exalts the effectiveness of the precedent catalyst. The amount of the inorganic powder to be added is not easily defined uniquely because it is variable with such factors as size distribution, shape of particles, and specific surface area. The catalytically active substance is desired to cover thoroughly the surfaces of particles of the inorganic powder. From this point of view, the amount is generally desired to be in the range of from 5% by weight to 1000% by weight, preferably from 10% by weight to 500% by weight, based on the weight of the catalytically active substance as an oxide. Incidentally, such an inorganic powder as titania which has been heretofore used in the catalyst for the production of pyromellitic anhydride has an ability to enhance the activity of vanadium and, consequently, degrade the selectivity of the precedent catalyst. Thus, it does not fit the purpose of use in a large amount enough to ensure thorough dispersion of the catalytically active substance.

The third catalyst (C) is not particularly restricted as to the method for preparation or the raw material. It can be prepared by any of the methods which have been generally adopted heretofore. It can be prepared from such raw materials as nitrates, carbonates, and organic acid salts which are decomposed by heating into respective oxides. For the oxide powder to be used for the third catalyst (C) is required to have high purity, it may be prepared from a corresponding salt prior to the preparation of a relevant catalyst, calcined, and then incorporated in the form of a calcined oxide powder in the prepared catalyst. The necessity for this deliberate preparation of the calcined oxide powder is obviated when such a natural mineral as diatomaceous earth is used. As respects the method for the preparation of the catalyst, the component elements are desired to be mixed as uniformly as possible. Specifically, the catalyst is produced by mixing or kneading by the use of a stirrer the components prepared in a prescribed formulation in such a solvent as water and depositing the resultant liquid or slurry mixture on a carrier. In this case, the method which enhances the strength with which the slurry mixture is deposited on the carrier by adding whiskers or other similar fibrous substance to the slurry may be used favorably.

The third catalyst (C) may use a carrier. Any of the inert carriers of the common run can be used. Preferably, an inorganic porous carrier which has an apparent porosity in the range of from 5 to 50%, a BET specific surface area of not more than 5 $m^2/g$, preferably from 0.05 to 1 $m^2/g$, an aluminum content of not more than 10% by weight, preferably not more than 3% by weight, and a SiC content of not less than 50% by weight, preferably not less than 80% by weight is used. A self-sintering type porous SiC carrier having an assay of about 98% is advantageously used. The form of the carrier to be used for the third catalyst (C) is not particularly restricted. The carrier may be in any of various forms such as, for example, spheres, rings, cylinders, cones, and saddles. For the carrier to be advantageously used, the apparent outside diameter thereof is desired to be in the range of from 3 to 15 mm, preferably from 3 to 10 mm, on the average.

The deposition of the active substance for the third catalyst (C) on the carrier thereof may be effected by any of the well-known methods such as, for example, the spray deposition method and the impregnation deposition method. Preferably, this deposition of the active substance is carried out by spraying the catalyst solution or catalyst slurry on the carrier which is kept heated at a temperature in the range of from 90° to 200° C. The amount of the active substance for the catalyst to be deposited is in the range of from 3 to 100 g, preferably from 10 to 70 g, per 100 cc of the apparent volume of the carrier. The active substance thus deposited on the carrier is calcined at a temperature in the range of from 400° to 700° C., preferably from 500° to 650° C., for a period in the range of from 1 to 10 hours, preferably from 2 to 6 hours, to obtain the catalyst.

The third catalyst (C) which is prepared as described above and intended as a precedent catalyst functions to repress the formation of a combustion gas to an extremely low level, ensures the formation of an intermediate oxide as the precursor of pyromellitic anhydride, and feeds this intermediate oxide to the catalyst which is packed in the rearward part. When a tetraalkyl benzene is passed through the precedent catalyst alone, it forms practically no pyromellitic anhydride and nevertheless undergoes a conversion at a ratio of some tens of percent. When the precedent catalyst is disposed on the raw material mixed gas inlet side of the first catalyst (A), the yield of the pyromellitic anhydride increases in proportion as the ratio of conversion in the precedent catalyst part rises under relevant reaction conditions. This fact indicates that the precedent catalyst manifests an ability to form an intermediate oxide which serves as a pyromellitic anhydride precursor capable of being converted into pyromellitic anhydride at a high selectivity.

Further, in any of the above mention first, second and catalysts, the catalyst can be used in normal state, and for example, a supported type catalyst wherein a catalytic substance is supported on an inert carrier and a formed type catalyst wherein a catalytic substance is formed in a desired shape can be used, and the supported type catalyst is preferable.

As respects the reaction conditions in this invention, the heat medium is kept at a temperature in the range of from 340° to 460° C., preferably from 360° to 440° C. If the temperature exceeds the upper limit of this range, the conversion is unduly large and the yield unduly low. If it is short of the lower limit of the range, the unaltered by-product is so large as to lower the yield and degrade the quality of the product. The reaction tube to be used for this invention is required to have an inside diameter in the range of from 15 to 40 mm, preferably from 15 to 30 mm. The effectiveness with which the heat of reaction is removed exalts in proportion as the diameter of the reaction tube decreases. If the diameter is unduly small, however, the reaction tube obstructs the work of packing the catalyst.

The raw material mixed gas of this invention is a mixture of a molecular oxygen—containing gas with a tetraalkyl benzene of a concentration in the range of from 10 to 100 g/Nm$^3$, preferably from 20 to 50 g/Nm$^3$. If the concentration of the tetraalkyl benzene in the raw material mixed gas is short of the lower limit of the range mentioned above, the production of pyromellitic anhydride will be impracticable because of unduly low productivity of the reaction involved.

Although space velocities to each catalysts are as mentioned above, the space velocity to whole such multi layered catalyst is preferably 1,000 to 15,000 hr$^{-1}$, more preferably 3,000 to 10,000 hr$^{-1}$.

Raw material mixed gas in the present invention is a gas obtained by mixing a molecular oxygen containing as with tetraalkyl benzene in a amount of 10 to 100 g/Nm$^3$, more preferably 20 to 50 g/Nm$^3$. If the concentration of tetraalkyl benzene in the raw material mixed gas is lower than such concentration, productivity decreases, so it is not practical. Further, if it is more than such concentration, an amount of the heat generation increases, so it is not preferable in respect of yield and life of life.

The oxygen concentration in the molecular oxygen-containing gas to be used for the reaction naturally must be enough for the formation of pyromellitic anhydride from the tetraalkyl benzene. Actually, it is sufficient to use air. The space velocity of the raw material mixed gas is as already mentioned. It can be suitably determined depending on the method for superposition of the component catalysts.

Durene is a typical example of the tetraalkyl benzene which is used as the raw material in this invention.

Now, the method of this invention will be more specifically described below with reference to referential examples and working examples. Further, titanium dioxide used in Referential Examples and Examples are anatase type titanium dioxide having 20 m$^2$/g of BET specific surface area.

REFERENTIAL EXAMPLE 1

A catalytic component slurry 900 ml in volume was prepared by dissolving 240 g of oxalic acid in 700 ml of deionized water, uniformly mixing the resultant aqueous solution with 120 g of ammonium metavanadate and 18.1 g of ammonium molybdate, then uniformly mixing the resultant mixture with 3.54 g of ammonium primary phosphate, and further thoroughly stirring to emulsify the produced mixture with 260 g of titanium oxide and 20 g of silicon carbide whiskers until a uniform slurry was formed. In an externally heating rotary furnace, 200 ml of SiC carrier spheres having an average particle diameter of 4 mm were preheated to a temperature in the range of from 200° to 350° C. The catalytic component slurry prepared as described above was sprayed onto the preheated SiC carrier to deposit 10 g of the catalytic substance thereon. Subsequently, the catalytic substance deposited on the carrier was calcined in a calcination furnace at 500° C. for 6 hours to obtain Catalyst A1.

REFERENTIAL EXAMPLE 2

A catalytic component slurry 900 ml in volume was prepared by dissolving 240 g of oxalic acid in 700 ml of deionized water, uniformly mixing the resultant aqueous solution with 120 g of ammonium metavanadate and 18.1 g of ammonium molybdate, then uniformly mixing the resultant mixture with 3.54 g of ammonium primary phosphate and 8.71 g of silver nitrate dissolved in advance in a small amount of deionized water, and further mixing the produced mixture with 20 g of silicon carbide whiskers. In an externally heating rotary furnace, 200 ml of SiC carrier spheres having an average particle diameter of 4 mm were preheated to a temperature in the range of from 200° to 350° C. The catalytic component slurry prepared as described above was sprayed onto the preheated SiC carrier to deposit 10 g of the catalytic substance thereon. Subsequently, the catalytic substance deposited on the carrier was calcined in a calcination furnace at 500° C. for 6 hours to obtain Catalyst A2.

REFERENTIAL EXAMPLE 3

Catalyst A3 was prepared by following the procedure of Referential Example 2 while using 23.8 g of an aqueous ammonium metatungstate solution containing 50% by weight of tungsten oxide in the place of ammonium molybdate.

REFERENTIAL EXAMPLE 4

Catalyst A4 was prepared by following the procedure of Referential Example 2 while adding 4.85 g of calcium nitrate prior to the addition of silver nitrate.

REFERENTIAL EXAMPLE 5

Catalyst A5 was prepared by following the procedure of Referential Example 2 while adding 0.174 g of sodium nitrate prior to the addition of silver nitrate.

REFERENTIAL EXAMPLE 6

Catalyst A6 was prepared by following the procedure of Referential Example 2 while changing the amount of ammonium molybdate to be added to 90.6 g.

REFERENTIAL EXAMPLE 7

Catalyst A7 was prepared by following the procedure of Referential Example 2 while changing the amount of ammonium molybdate to be added to 452 g and diluting the chemical liquid to 1500 ml.

REFERENTIAL EXAMPLE 8

Catalyst A8 was prepared by following the procedure of Referentional Example 1 while further adding 8.71g of silver nitrate dissolved in advance in a small amount of deionized water. The compositions of Catalysts A1 through A8 obtained in Referential Examples 1 through 8 are shown in Table 1 below.

TABLE 1

| Referential Example | Name of Catalyst | Composition of Catalyst | | |
|---|---|---|---|---|
| | | V | Mo or W | Other element |
| 1 | A1 | 1 | Mo (0.1) | P (0.03), $TiO_2$ (4500) |
| 2 | A2 | 1 | Mo (0.1) | P (0.03), Ag (0.05) |
| 3 | A3 | 1 | W (0.05) | P (0.03), Ag (0.05) |
| 4 | A4 | 1 | Mo (0.1) | P (0.03), Ag (0.05), Ca (0.02) |
| 5 | A5 | 1 | Mo (0.1) | P (0.03), Ag (0.05), Na (0.002) |
| 6 | A6 | 1 | Mo (0.5) | P (0.03), Ag (0.07) |
| 7 | A7 | 1 | Mo (2.5) | P (0.03), Ag (0.05) |
| 8 | A8 | 1 | Mo (0.1) | P (0.03), Ag (0.05) $TiO_2$ (4500) |

In the column "composition of catalyst," V is vanadium, Mo is molybdenum, and W is tungsten, other element refers to element other than V, Mo, and W contained in the catalyst composition, and the numeral enclosed with parentheses represents an atomic ratio.

In the case of $TiO_2$, however, the numeral enclosed with parentheses represents the surface area of vanadium and molybdenum per mol of element.

Controls 1 through 8

Catalysts A1 through A8 obtained in Referential Examples 1 through 8 were severally packed in a bed length of 150 mm in reaction vessels measuring 20 mm in inside diameter and 400 mm in length and made of stainless steel. The same catalysts were diluted for the purpose of lowering the temperature of heat point with an equal weight of SiC carrier spheres having an average particle diameter of 4 mm and were packed in a bed length of 50 mm, and glass beads having average particle diameter of 5 mm were packed in a bed length of 150 mm.

A raw material mixed gas which was composed of durene of a concentration of 20 g/$Nm^3$ and the balance of air was passed through the catalyst beds at a flow volume of 6.3 liters/min and at a space velocity of 6,000 $hr^{-1}$ to carry out a reaction. The reaction temperatures were severally optimized for the catalysts. The produced reaction gases were collected in an air-cooled crystallizing glass tube and two scrubbing bottles filled with deionized water and analyzed by liquid chromatography to determine the yield of pyromellitic acid and find the yield of pyromellitic anhydride by computation. The results were as shown in Table 2 below.

TABLE 2

| Control | Name or Catalyst | Space Velocity ($hr^{-1}$) | Reaction Temperature (°C.) | Conversion (mol %) | Yield of PMDA* (mol %) |
|---|---|---|---|---|---|
| 1 | A1 | 6,000 | 395 | 100.0 | 60.5 |
| 2 | A2 | 6,000 | 400 | 100.0 | 59.3 |
| 3 | A3 | 6,000 | 410 | 100.0 | 59.5 |
| 4 | A4 | 6,000 | 405 | 100.0 | 61.7 |
| 5 | A5 | 6,000 | 405 | 100.0 | 61.5 |
| 6 | A6 | 6,000 | 420 | 100.0 | 61.5 |
| 7 | A7 | 6,000 | 430 | 100.0 | 54.7 |
| 8 | A8 | 6,000 | 390 | 100.0 | 62.9 |

*PMDA: Pyromellitic anhydride (same in the following tables).

REFERENTIAL EXAMPLE 9

A catalytic component slurry about 900 ml in volume was prepared by dissolving 56 g of oxalic acid in 350 ml of deionized water, uniformly mixing the resultant aqueous solution with 28 g of ammonium metavanadate, then uniformly mixing the resultant mixture with 10.5 g of antimony trioxide, and further uniformly mixing the produced mixture with 239 g of titanium oxide and further with deionized water. In an externally heating rotary furnace, 200 ml of self-sintering type silicon carbide carrier spheres having an average particle diameter of 4 mm were preheated to a temperature in the range of from 150° to 250° C. The catalytic component slurry prepared as described above was sprayed onto the preheated SiC carrier to deposit 15 g of the catalytic substance thereon. Subsequently, the catalytic substance deposited on the carrier was calcined in a calcination furnace at 550° C for 6 hours to obtain Catalyst B1.

REFERENTIAL EXAMPLE 10

Catalyst B2 was prepared by following the procedure of Referential Example 9 while decreasing the deionized water to a half amount and using 1.38 g of ammonium primary phosphate in the place of antimony trioxide and changing the amount of titanium oxide to 115 g.

REFERENTIAL EXAMPLE 11

Catalyst B3 was prepared by following the procedure of Referential Example 10 while adding 4.53 g of antimony trioxide prior to the addition of titanium oxide.

REFERENTIAL EXAMPLE 12

Catalyst B4 was prepared by following the procedure of Referential Example 11 while increasing the deionized water to 4 times and changing the amount of titanium oxide to be added to 460 g.

REFERENTIAL EXAMPLE 13

Catalyst B5 was prepared by following the procedure of Referential Example 9 while adding 0.85 g of ammonium molybdate after the addition of ammonium primary phosphate.

The compositions of Catalysts B1 through B5 obtained in Referential Examples 9 through 13 are shown in Table 3 below.

TABLE 3

| Referential Example | Name of Catalyst | Composition of Catalyst | | |
|---|---|---|---|---|
| | | V | Mo | Other element |
| 9 | B1 | 1 | 0 | Sb (0.3), TiO$_2$ (19,200) |
| 10 | B2 | 1 | 0 | P (0.05), TiO$_2$ (9,600) |
| 11 | B3 | 1 | 0 | P (0.05), Sb (0.13), TiO$_2$ (9,600) |
| 12 | B4 | 1 | 0 | P (0.05), Sb (0.13), TiO$_2$ (38,400) |
| 13 | B5 | 1 | 0.02 | Sb (0.03), TiO$_2$ (19,200) |

In the column "composition of catalyst," V is vanadium, Mo is molybdenum, and W is tungsten, other element refers to element other than V, Mo, and W contained in the catalyst composition, and the numeral enclosed with parentheses represents an atomic ratio.

In the case of TiO$_2$, however, the numeral enclosed with parentheses represents the surface area of vanadium and molybdenum per mol of element. Controls 9 through 13 Catalysts B1 through B5 obtained in Referential Examples 9 through 13 were severally packed in a bed length of 150 mm in reaction vessels measuring 20 mm in inside diameter and 400 mm in length and made of stainless steel. The same catalysts were diluted for the purpose of lowering the temperature of heat point with an equal weight of SiC carrier spheres having an average particle diameter of 4 mm were packed in a bed length of 50 mm, glass beads having average particle diameter of 5 mm was packed in a bed length of 150 mm.

A raw material mixed gas which was composed of durene of a concentration of 20 g/Nm$^3$ and the balance of air was passed through the catalyst beds at a flow volume of 6.3 liters/min. and a space velocity of 6,000 hr$^{-1}$ to carry out a reaction. The reaction temperatures were severally optimized for the catalysts. The produced reaction gases were collected in an air-cooled crystallizing glass tube and two scrubbing bottles filled with deionized water and analyzed by liquid chromatography to determine the yield of pyromellitic acid and find the yield of pyromellitic anhydride by computation. The results were as shown in Table 4 below.

TABLE 4

| Control | Name or Catalyst | Space Velocity (hr$^{-1}$) | Reaction Temperature (°C.) | Conversion (mol %) | Yield of PMDA* (mol %) |
|---|---|---|---|---|---|
| 9 | B1 | 6,000 | 380 | 100.0 | 58.8 |
| 10 | B2 | 6,000 | 380 | 100.0 | 59.7 |
| 11 | B3 | 6,000 | 380 | 100.0 | 60.8 |
| 12 | B4 | 6,000 | 380 | 100.0 | 56.5 |
| 13 | B5 | 6,000 | 390 | 100.0 | 59.5 |

REFERENTIAL EXAMPLE 14

A chemical liquid was prepared by adding 93 g of ammonium metavanadate to 450 ml of deionized water and then to 46 g of 85% phosphoric acid to form a homogeneous solution, thoroughly stirring the solution with 48.2 g of potassium nitrate and 65 g of diatomaceous earth (Snlow Floss, product of mamiclle Co.) to form a homogeneous catalytic component slurry, and diluting the slurry with deionized water to a total volume of 900 ml. In an externally heating rotary furnace, 200 g of self-sintering type SiC carrier spheres having an average particle diameter of 4 mm were preheated to a temperature in the range of from 100° to 250° C. The catalytic component slurry prepared as described above was sprayed onto the preheated SiC carrier to deposit 50 g of the catalytic substance thereon. Subsequently, the catalytic substance deposited on the carrier was calcined under a current of air at 610° C. for 6 hours to obtain Catalyst C1.

REFERENTIAL EXAMPLE 15

Catalyst C2 was prepared by following the procedure of Referential Example 14 while adding 24.1 g of potassium nitrate and 46.5 g of cesium nitrate in the place of potassium nitrate and thereafter adding 19.2 g of copper nitrate (trihydrate).

REFERENTIAL EXAMPLE 16

Catalyst C3 was prepared by following the procedure of Referential Example 15 while changing the amount of potassium sulfate to 20.8 g and the amount of cesium sulfate to 43.2 g, adding copper nitrate, and thereafter adding 14.0 g of ammonium molybdate.

REFERENTIAL EXAMPLE 17

Catalyst C4 was prepared by following the procedure of Referential Example 14 while changing the amount of potassium nitrate to 241.1 g.

REFERENTIAL EXAMPLE 18

Catalyst C5 was prepared by following the procedure of Referential Example 14 while changing the amount of potassium nitrate to 2.4 g.

REFERENTIAL EXAMPLE 19

Catalyst C6 was prepared by following the procedure of Referential Example 15 while changing the amount of copper nitrate to 384.1 g and diluting the chemical liquid with deionized water to a total volume of 1400 ml.

The compositions of Catalysts C1 through C6 obtained in Referential Example 14 through 19 are shown in Table 5.

TABLE 5

| Referential Example | Name of Catalyst | Composition of Catalyst | | |
|---|---|---|---|---|
| | | V | Alkali Metal | Other element |
| 14 | C1 | 1 | K (0.6) | P (0.5) |
| 15 | C2 | 1 | K (0.3), Cs (0.3) | P (0.5), Cu (0.1) |
| 16 | C3 | 1 | K (0.3), Cs (0.3) | P (0.5), Cu (0.1), S (0.3), Mo (0.1) |
| 17 | C4 | 1 | K (3) | P (0.5) |
| 18 | C5 | 1 | K (0.03) | P (0.5) |
| 19 | C6 | 1 | K (0.3), Cs (0.3) | P (0.5), Cu (2.0) |

In the column "composition of catalyst," V is vanadium and other element refers to element other than contained in the catalyst composition, and the numeral enclosed with parentheses represents an atomic ratio. Examples 1 through 4

In a reaction tube made of stainless steel and measuring 20 mm in inside diameter and 400 mm in length, Catalyst A4 obtained in Referential Example 4 was packed on the reaction gas outlet side and Catalysts C1 through C3 obtained in Referential Examples 14 through 16 were severally packed on the raw material mixed gas inlet side in bed lengths indicated in Table 6. Glass beads having average particle diameter of 5 mm were packed in a bed length of 150 mm at a reaction gas inlet side.

Through the catalyst beds thus obtained, a raw material mixed gas composed of durene of a concentration of 20 g/Nm$^3$ and the balance of air was passed at a flow volume of 6.3 liters/min. and a space velocity of 4,000 hr$^{-1}$ to carry out a reaction. The reaction temperatures were severally optimized for the catalysts. The produced reaction gases were collected in an air-cooled crystallizing glass tube and two scrubbing bottles filled with deionized water and analyzed by liquid chromatography to determine the yield of pyromellitic acid and find the yield of pyromellitic anhydride by computation. The results were as shown in Table 6 below.

TABLE 6

Superposed Layer of Third Catalyst (C) - First Catalyst (A)

| Example | Length of Catalyst (C) Layer (mm) | Length of Catalyst (A) Layer (mm) | Space Velocity (hr$^{-1}$) | Reaction Temperature (°C.) | Yield of PMDA* (mol %) |
|---|---|---|---|---|---|
| 1 | C1 100 | A4 200 | 4,000 | 430 | 64.3 |
| 2 | C2 100 | A4 200 | 4,000 | 420 | 66.6 |
| 3 | C3 100 | A4 200 | 4,000 | 410 | 67.8 |
| 4 | C3 150 | A4 200 | 3,400 | 410 | 68.5 |

Controls 14 through 16

The procedures of Examples 1 through 4 were repeated except that Catalyst A4 obtained in Referential Example 4 was packed on the reaction gas outlet side of the reaction tube and Catalysts C4 through C6 obtained in Referential Examples 17 through 19 were severally packed on the raw material mixed gas inlet side in bed lengths indicated in Table 7. The results were as shown in Table 7.

TABLE 7

Superposed Layer of Third Catalyst (C) - First Catalyst (A)

| Control | Length of Catalyst (C) Layer (mm) | Length of Catalyst (A) Layer (mm) | Space Velocity (hr$^{-1}$) | Reaction Temperature (°C.) | Yield of PMDA* (mol %) |
|---|---|---|---|---|---|
| 13 | C4 100 | A4 200 | 4,000 | 405 | 61.5 |
| 14 | C5 100 | A4 200 | 4,000 | 400 | 59.3 |
| 15 | C6 100 | A4 200 | 4,000 | 405 | 61.7 |

Examples 5 through 15 and Control 17

The procedures of Examples 1 through 4 were repeated except that Catalysts A8 through A7 obtained in Referential Example 1 through 8 were severally packed on the reaction gas outlet side of the reaction tube and Catalysts B1 through B7 obtained in Referential Examples 9 through 13 were severally packed on the raw material mixed gas inlet side in bed lengths indicated in Table 8. The results were as shown in Table 8.

TABLE 8

Superposed Layer of Second Catalyst (B) - First Catalyst (A)

| Example | Length of Catalyst (B) Layer (mm) | Length of Catalyst (A) Layer (mm) | Space Velocity (hr$^{-1}$) | Reaction Temperature (°C.) | Yield of PMDA* (mol %) |
|---|---|---|---|---|---|
| 5 | B1 50 | A4 150 | 6,000 | 410 | 69.1 |
| 6 | B2 50 | A4 150 | 6,000 | 410 | 65.5 |
| 7 | B3 50 | A4 150 | 6,000 | 410 | 66.5 |
| 8 | B4 50 | A4 150 | 6,000 | 410 | 66.7 |
| 9 | B5 50 | A4 150 | 6,000 | 410 | 67.1 |
| 10 | B4 50 | A1 150 | 6,000 | 400 | 64.8 |
| 11 | B4 50 | A2 150 | 6,000 | 410 | 65.6 |
| 12 | B4 50 | A3 150 | 6,000 | 420 | 65.8 |
| 13 | B4 50 | A5 150 | 6,000 | 410 | 66.5 |
| 14 | B4 50 | A6 150 | 6,000 | 420 | 65 |
| 15 | B4 50 | A8 150 | 6,000 | 400 | 65.8 |
| Control 17 | B4 50 | C7 150 | 6,000 | 420 | 58.2 |

Example 16

The procedure of Example 1 was repeated except that Catalyst A4 obtained in Referential Example 4 was packed on the reaction gas outlet side of the reaction tube, Catalysts C3 obtained in Referential Example 16 was packed on the raw material mixed gas inlet side, and Catalyst B5 obtained in Referential Example 13 was packed between Catalyst A4 and Catalyst C3 in bed lengths indicated in Table 9. The results were as shown in Table 9.

TABLE 9

| | Superposed Layer of Third Catalyst (C) - Second Catalyst (B) - First Catalyst (A) | | | | | |
|---|---|---|---|---|---|---|
| Example | Length of Catalyst (C) Layer (mm) | Length of Catalyst (B) Layer (mm) | Length of Catalyst (A) Layer (mm) | Space Velocity ($hr^{-1}$) | Reaction Temperature (°C.) | Yield of PMDA* (mol %) |
| 16 | C3<br>50 | B5<br>50 | A4<br>150 | 4,800 | 410 | 68.5 |

Example 17

Catalysts C7, B6, and A9 were prepared by depositing the active components prepared in the same formulations as in Catalysts C2, B4, and A4 in the same manner on tubular SiC carriers having an average outside diameter of about 7 mm, an inside diameter of 4 mm, and a length of 7 mm. In a reaction tube having an inside diameter of 25 mm and immersed in a total length of 4000 mm in a molten salt bath, 1700 mm of Catalyst A9 was packed and 800 mm of Catalyst B6 diluted at a ratio of 1/2.5 with 1.5 times its weight of tubular SiC carriers was packed on the raw material gas inlet side. Further, Denstone carrier (product of Norton Company) was packed on the reaction gas inlet side. A raw material gas containing durene gas at a concentration of 30 g/Nm³ was passed through the reaction tube at a space velocity of 6000 $hr^{-1}$ to effect a reaction. The reaction gas was sampled in a size of 100 liters and analyzed in the same manner as in Examples 1 through 4. It was consequently found that the yield of pyromellitic anhydride was 66.3 mol % when the temperature of the molten salt was 395° C. The same reaction gas was collected with a collecting device having the wall surface temperature thereof kept at 150° C. to obtain white crystals. A solution of 0.5 g of these white crystals in 50 ml of dimethyl sulfoxide was tested for Klett value by the use of a Klett tester (produced by Klett-Summerson Corp. and marketed under product code of "Model 800-3"). The solution was found to have a Klett value of 130.

The catalyst bed mentioned above had 500 mm of Catalyst C7 additionally packed on the raw material gas inlet side of the reaction tube, and Denstone carrier was similarly packed on the reaction gas inlet side, and then tested for reaction in the same manner as mentioned above.

The yield of pyromellitic anhydride was 67.5 mol % when the molten salt temperature was 395° C. and the Klett value was 100.

The combined catalyst system of this invention exhibits high quality even when it is used in a reaction vessel of commercial scale and the third catalyst (C) clearly manifests an effect of repressing the coloration of product as described above.

Example 18

In the same combined catalyst system using Catalysts B4 and A2 as in Example 11, 100 mm of Catalyst B4 was packed on the reaction gas outlet side of the catalyst bed and the same raw material gas containing durene at the same concentration was passed through the reaction tube at the same flow volume and caused to react at the same temperature to evaluate the reaction. Thus, the yield of pyromellitic anhydride was 63.5 mol %, i.e. a decline of about 2 mol % in yield. Then, the same evaluation was carried out by following the same procedure while using 100 ml of Catalyst A2 in the place of Catalyst B4.

As a result, the yield of pyromellitic anhydride was found to be 65.5 mol %, i.e. no decline in yield.

The decline of yield is thought to result from reoxidation of pyromellitic anhydride. It is further thought that Catalyst A2 exhibits fairly low reoxidizing power to pyromellitic anhydride as compared with Catalyst B4. When these catalysts are used in the form of independent beds, the effect brought about by this reoxidization is believed to be actually larger because the reaction in the neighborhood of a hot point is performed at a higher temperature than is involved in the conditions mentioned above. In the light of all these factors, it is concluded that the post-stage catalyst containing molybdenum advantageously functions when it is packed in the rear part of the catalyst bed through which the reaction gas containing pyromellitic anhydride in a larger concentration is passed.

Example 19 and 20

In a combination of the catalyst B4 with the catalyst A2 in Example 11, the procedure of Example 11 was repeated except that the layer length ratio of the layer of the catalyst B4 to the layer of the catalyst A2 was changed. As the catalyst layer using catalyst B4, the catalyst layer diluted with the same amount of the carrier was used and the catalyst layer using the catalyst A4 was not diluted with the carrier. The results were as shown in Table 10.

In Example 19 wherein the layer length of the catalyst B4 is longer in an amount of 40% than that in Example 11, difference of yield was almost not found. Further, in Example 20 wherein the layer length of the catalyst B4 is shorter in an amount of 40% than that of Example 11, an optimum reaction temperature increased, and the yield decreased compared to Example 11. And in Example 20, maximum temperature zone of the catalyst resided in a level of the catalyst A2. The results were as shown in Table 10.

Example 21

In a combination of the catalyst B3 with the catalyst A4, the procedure of Example 7 was repeated except that 50 mm of a front portion of the layer of the catalyst A4 was substituted by the catalyst B3. That is, the reaction was carried out using catalyst layers packed with mm of a catalyst layer comprising the diluted catalyst B3 plus 50 mm of a catalyst layer comprising the non-diluted catalyst B3 plus 100 mm of a catalyst layer comprising the catalyst A4 from the reaction gas inlet side. The results were as shown in Table 10.

TABLE 10

| Example | Length of Catalyst (B) Layer (mm) | Length of Catalyst (C) Layer (mm) | Space Velocity (hr$^{-1}$) | Reaction Temperature (°C.) | Yield of PMDA* (mol %) |
| --- | --- | --- | --- | --- | --- |
| 19 | B4 30 | A2 170 | 6,000 | 420 | 64.2 |
| 20 | B4 70 | A2 130 | 6,000 | 400 | 65.7 |
| 21 | B3 100 | A2 100 | 6,000 | 400 | 54 |

What is claimed is:

1. A method for the production of pyromellitic anhydride by the catalytic vapor-phase oxidation of a raw material mixed gas comprising a tetraalkyl benzene and a molecular oxygen-containing gas by the use of a fixed-bed shell-and-tube type reaction vessel, which comprises using a multi-layer catalyst obtained by dividing a catalyst layer to be used in the reaction vessel into at least two layers, packing the formed gas outlet side thereof with a first catalyst containing vanadium (a) and at least one metal (b) selected from the group consisting of molybdenum and tungsten and having an atomic ratio of the metal (b) to vanadium (a) in the range of from 0.01 to 2, and packing the raw material mixed gas inlet side thereof with at least one other species of catalyst selected from the group consisting of a second catalyst containing vanadium (a) and at least one metal (b) selected from the group consisting of molybdenum and tungsten and having an atomic ratio of the metal (b) to vanadium (a) smaller than said first catalyst and a third catalyst containing vanadium (a) and an alkali metal (c) and having a ratio of the alkali metal (c) to vanadium (a) in the range of from 0.2 to 2.5.

2. A method according to claim 1, wherein a packed volume of said first catalyst is greater than a packed volume of said second catalyst.

3. A method according to claim 1, wherein said first catalyst further contains silver and the atomic ratio of silver to vanadium is in the range of from 0.001 to 0.2.

4. A method according to claims 1, wherein said first catalyst further contains at least one metal selected from the group consisting of alkali metals and an alkaline earth metals and the atomic ratio of said metal to vanadium is in the range of from 0.001 to 0.1.

5. A method according to claims 1, wherein said first catalyst further contains at least one element selected from the group consisting of phosphorus, antimony, boron, chromium, cerium, and sulfur and the atomic ratio of said element to vanadium is in the range of from 0.002 to 1.

6. A method according to claims 1, wherein the catalytically active component in said first catalyst is dispersed in a powder or whiskers of an inorganic oxide.

7. A method according to claim 1, wherein the catalytically active component of said second catalyst is dispersed in a powder or whiskers of an inorganic oxide.

8. A method according to claims 1, wherein said second catalyst further contains at least one element selected from the group consisting of phosphorus, antimony, boron, chromium, cerium, and sulfur and the atomic ratio of said element o vanadium is in the range of from 0.002 to 1.

9. A method according to claim 1, wherein the third catalyst further contains at least one element selected from the group consisting of phosphorus and copper, and the atomic ratio of the element to vanadium is in the range of more than 0 to not more than 2.

10. A method according to claim 1, wherein said third catalyst further contains at least one element selected from the group consisting of silver, sulfur, boron, tantalum, and molybdenum and the atomic ratio of said element to vanadium is in the range of from 0.01 to 2.

11. A method according to claim 1, wherein the concentration of tetraalkyl benzene in the raw material mixed gas is in the range of from 10 to 100 g/Nm$^3$ and the reaction temperature is in the range of from 340° to 460° C.

12. A method according to claim 1, wherein said first catalyst is packed in such an amount as to allow a space velocity in the range of from 2,000 to 20,000 hr$^{-1}$, said second catalyst is packed in such an amount as to allow a space velocity in the range of from 10,000 to 50,000 hr$^{-1}$, and said third catalyst is packed in such an amount as to allow a space velocity in the range of from 500 to 50,000 hr$^{-1}$.

13. A method according to claim 11, wherein a space velocity to whole multi layered catalyst is 1,000 to 15,000 hr$^{-1}$.

14. A method according to claim 1, wherein a length ratio of said second catalyst layer /said first catalyst layer is in the range of 1/10 though 1/1.

15. A method according to claim 1, wherein a length ratio of said third catalyst layer/said first catalyst layer is in the range of not less than 1/5.

* * * * *